(12) United States Patent
Sommerlade et al.

(10) Patent No.: US 6,660,860 B2
(45) Date of Patent: Dec. 9, 2003

(54) PROCESS FOR THE SELECTIVE OXIDATION OF ALCOHOLS USING READILY REMOVABLE NITROXYL RADICALS

(75) Inventors: Reinhard Sommerlade, Freiburg (DE); Hansjörg Grützmacher, Wettswil (CH); Souâd Boulmaâz, Birsfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/164,768

(22) Filed: Jun. 7, 2002

(65) Prior Publication Data

US 2002/0161265 A1 Oct. 31, 2002

Related U.S. Application Data

(62) Division of application No. 09/713,277, filed on Nov. 15, 2000, now Pat. No. 6,441,243.

(30) Foreign Application Priority Data

Nov. 19, 1999 (CH) ................................ 2113/99

(51) Int. Cl.$^7$ ................ C07F 9/06; C07F 9/28; C07C 45/00
(52) U.S. Cl. ................ 546/23; 546/24; 546/25; 568/322
(58) Field of Search .............. 546/23, 24, 25; 568/322

(56) References Cited

U.S. PATENT DOCUMENTS 5,856,584 A   1/1999  Prakash et al.

FOREIGN PATENT DOCUMENTS

WO          99/29646        6/1999

OTHER PUBLICATIONS

S. Rychnovsky et al., J. Org. Chem. (1999), vol. 64, pp. 310–312.
Chem. Abstr. 120:244345d (1994) for JP 05310632.
B. Hinzen et al., Synthesis, (1998), pp. 977–979.
L. Dulog et al., Makromol. Chem. vol. 189, pp. 2611–2615 (1988).
A. E. J. de Nooy et al, Synthesis, (1996), pp. 1153–1174.

Primary Examiner—Johann Richter
Assistant Examiner—Sikarl A. Witherspoon
(74) Attorney, Agent, or Firm—Tyler A. Stevenson

(57) ABSTRACT

The invention relates to a process for the selective oxidation of alcohols to ketones or to aldehydes by means of an alkali hypohalite under alkaline conditions, which comprises carrying out the oxidation in the presence of a heterogeneous oxidation catalyst that is insoluble in the reaction medium and is selected from the group comprising the compounds of formula (I)

wherein n is a number from 3 to 3000; or
a 4-oxy-2,2,6,6-tetramethylpiperidin-1-oxyl that is 4-oxy-bound to a Merrifield polymer.

The invention relates also to the compounds of formulae (II) and (III) and to the use of the above-mentioned oxidation catalysts for the oxidation of alcohols.

1 Claim, No Drawings

PROCESS FOR THE SELECTIVE OXIDATION OF ALCOHOLS USING READILY REMOVABLE NITROXYL RADICALS

This is a divisional of application Ser. No. 09/713,277, filed Nov. 15, 2000 U.S. Pat. No. 6,441,243, The invention relates to a process for the selective oxidation of alcohols to aldehydes and to ketones using a readily removable heterogeneous oxidation catalyst based on a nitroxyl radical, and using an alkali hypohalite as oxidising agent.

Alcohols are one of the most important building blocks in organic synthesis. An extensive arsenal of preparative methods for producing them make primary and secondary alcohols ideal preliminary stages for the synthesis of aldehydes, ketones and carboxylic acids. Customary oxidising agents are heavy metal reagents, for example chromium(VI) compounds, lead(IV) compounds and ruthenium, manganese and vanadium compounds, peracids, activated dimethyl sulfoxide (DMSO) and hypervalent iodine compounds.

Selectivity is of primary importance in such oxidation processes. Further functional groups present in the molecule, such as, for example, double bonds, should generally not be affected under the conditions chosen. Often, the targeted oxidation of secondary alongside primary alcohol functions or vice versa is desired, without the respective other function being affected. In the synthesis of aldehydes from primary alcohols, carboxylic acids are often formed as by-products of the oxidation reaction (over-oxidation), and the oxidation of 1,2-diols or $\alpha$-hydroxyketones is frequently accompanied by C—C cleavage reactions. A further disadvantage of many oxidants is that they are frequently relatively awkward or difficult to prepare or handle; heavy-metal-containing reagents, especially, are moreover in most cases highly toxic and ecologically very harmful. Finally, however, the costs of an oxidation method are of decisive importance, especially when the intended use is industrial.

It is known that primary and secondary alcohols can be converted into the corresponding carbonyl compounds using aqueous sodium hypochlorite solution in the presence of catalytic amounts of organic nitroxyl radicals (A. E. J. de Nooy, A. C. Besemer, H. van Bekkum, *Synthesis*, 1996, 1153).

Hitherto such reactions—especially when 2,2,6,6-tetramethylpiperidin-1-oxyl (TEMPO) has been used—have predominantly been carried out in homogeneous phase. The reactions were carried out either stoichiometrically or catalytically in respect of TEMPO or the oxidation product resulting therefrom. The working up of the reaction products in such processes often proves to be awkward and involved, since a great deal of effort is required to remove the catalyst and its attendant products.

Oxidation processes that employ immobilised or readily removable nitroxyl compounds have not, however, been described hitherto.

It has now, surprisingly, been found that alcohols can be reacted with sodium hypochlorite, as oxidant, to produce the corresponding carbonyl compounds in good yields by using certain higher-molecular-weight or oligomeric or polymer-fixed 2,2,6,6-piperidin-1-oxyls as catalysts.

Aliphatic 1,3-diols can be reacted in the presence of an aldehyde or ketone under suitable experimental conditions, in basic medium, to form the corresponding cyclic acetals and ketals (1,3-dioxanes), respectively, directly. 1,5-Diols are reacted to form tetrahydropyran-2-ols or ethers thereof or to form tetrahydropyran-2-ones ($\delta$-valerolactones), according to the experimental conditions. Hydroxy functions in the $\alpha$-position to carboxy functions are not affected.

Addition of bromide which, in the case of oxidation using a hypochlorite/TEMPO system carried out homogeneously, results in an appreciable acceleration of the reaction (S. D. Rychnovsky, R. Vaidyanathan, *J. Org. Chem.*, 1999, 64, 310), can be dispensed with in this process without any disadvantage. The merits of the present process lie in the simplified working up of the reaction batches, the repeated re-use of the catalyst and the omission of bromide as reaction-accelerating additive.

The invention relates to a process for the selective oxidation of alcohols to ketones or to aldehydes by means of an alkali hypohalite under alkaline conditions, which process comprises carrying out the oxidation in the presence of a heterogeneous oxidation catalyst that is insoluble in the reaction medium and is selected from the group comprising the compounds of formulae (I), (II), (III)

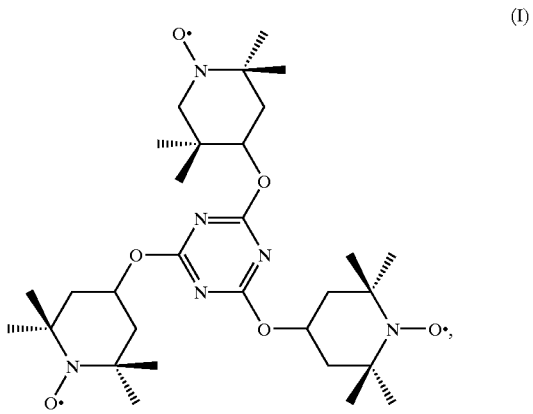

(I)

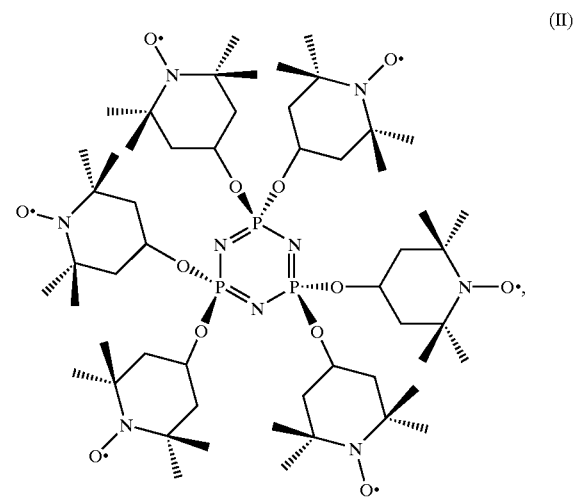

(II)

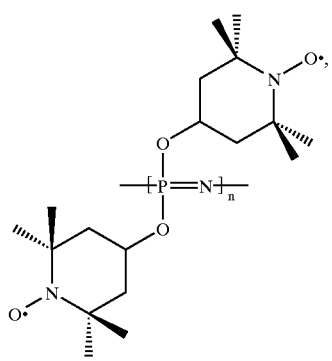

(III)

wherein n is a number from 3 to 3000; or
a 4-oxy-2,2,6,6-tetramethylpiperidin-1-oxyl that is 4-oxy-bound to a Merrifield polymer.

Preferably, n is a number from 10 to 1000, especially from 10 to 500 and more especially from 10 to 100.

Preference is given to a process that uses as the alkali hypohalite LiOCl, NaOCl, KOCl, LiOBr, NaOBr or KOBr.

LiOCl, NaOCl and KOCl are especially preferred, NaOCl being more especially preferred.

The oxidising agent is preferably added in the form of an aqueous solution to the alcohol to be oxidised. The concentration may vary within a wide range and is preferably from 5% to 20% by weight, especially from 10 to 15% by weight, of active chlorine based on the alcohol to be oxidised.

Together with the oxidising agent, the aqueous solution can be rendered alkaline by means of a base. Preferred bases are aqueous solutions of alkali or alkaline earth hydroxides, alkali or alkaline earth carbonates and the corresponding hydrogen carbonates.

Alkali hydrogen carbonates are especially preferred, sodium hydrogen carbonate being more especially preferred.

The pH value of the aqueous oxidation solution after the addition of the desired base is in the range from 8 to 12, especially in the range from 9 to 11 and more especially in the range from 9 to 10.

The alcohol to be oxidised may be liquid or solid. In the case of liquid alcohols, the reaction can be carried out without the addition of further solvents, but it can be advantageous to carry out the oxidation in a higher dilution. Solid alcohols always require a suitable organic solvent.

Suitable organic solvents or solvent mixtures are those which are water-immiscible. Examples include aliphatic hydrocarbons, aromatic hydrocarbons, chlorinated hydrocarbons or mixtures of such solvents with ketones, amides or esters.

Preferred solvents are aromatic hydrocarbons or mixtures thereof with ketones. Preferred examples include benzene, toluene and the isomers of xylene, which, if desired, can be mixed with acetone.

The mixing ratio can be from 10:1 to 2:1, but is preferably from 5:1 to 2:1.

Special preference is given to a mixture of toluene and acetone in a ratio of 3:1.

Preference is given to a process in which a 4-oxy-2,2,6,6-tetramethylpiperidin-1-oxyl that is 4-oxy-bound to a Merrifield polymer is used.

So-called Merrifield polymers are known to the person skilled in the art and are available commercially. In this connection, the Merrifield polymer is chloromethylated polystyrene that is partially crosslinked with divinylbenzene and therefore insoluble in conventional organic solvents.

The degree of crosslinking may be, for example, from 1 to 5%, and is typically from 1 to 2%. The particle size can vary within a wide range, and is typically from 100 to 400 mesh. The chlorine content is, for example, from 0.2 to 5 mmol/g; common polymers contain from 0.6 to 4 mmol/g.

The Merrifield polymer and the exchange of the chlorine atom can be represented diagrammatically as follows:

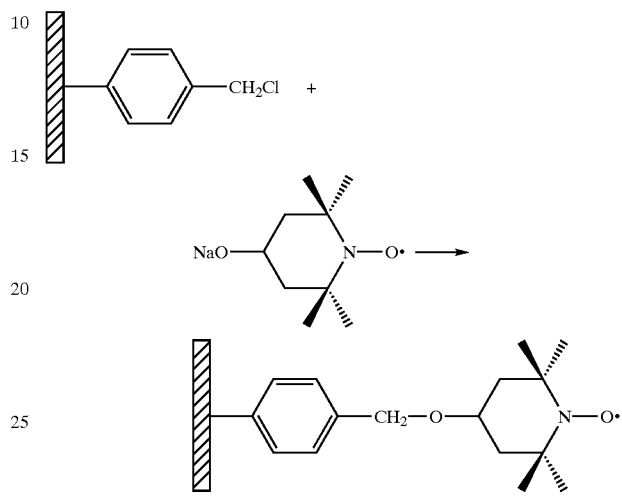

Preferably, the heterogeneous oxidation catalyst is added in an amount of from 0.1 to 20% by weight, especially from 1 to 10% by weight and more especially from 2 to 6% by weight, based on the alcohol used.

Preference is given to a process wherein a two-phase solvent system is used in which one phase is aqueous and comprises the oxidising agent.

Suitable solvents and solvent mixtures, including those which are preferred, have already been described hereinbefore.

Preferably, the reaction is carried out at a temperature of less than 10° C.

A temperature range of approximately from 0° C. to 10° C. is especially preferred.

The preparation of the compounds of formulae (I) to (III) and the preparation of the modified Merrifield polymer are carried out according to methods known per se in accordance with the reaction scheme hereinbelow.

In a first step, compound 3[4-hydroxy-2,2,6,6-piperidin-1-oxyl (4-hydroxy-TEMPO)] is reacted with sodium hydride. 4-Hydroxy-TEMPO itself is available commercially.

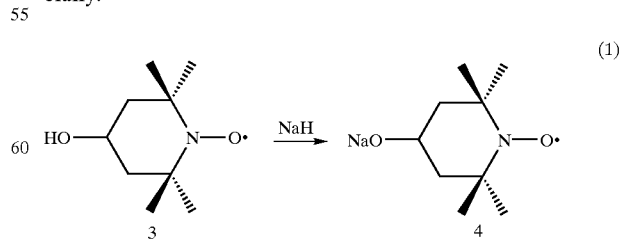

(1)

Compound 4 is further reacted in accordance with reaction 2, 3, 4 or 5, according to the desired end product.

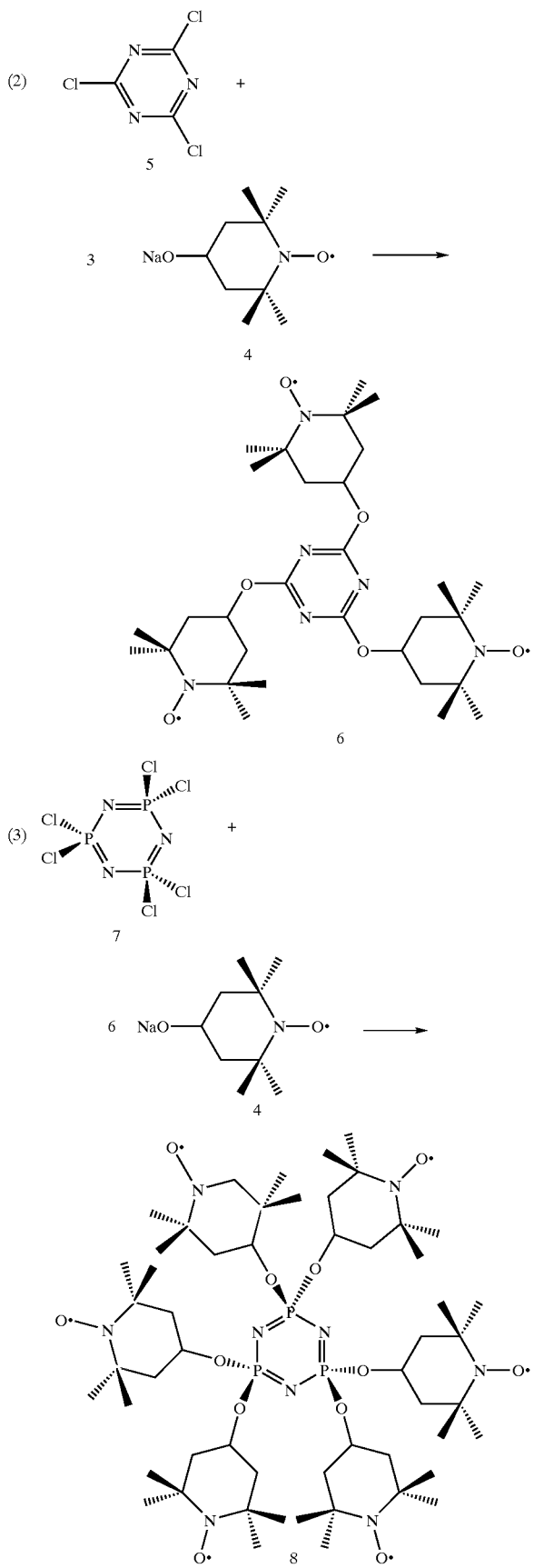

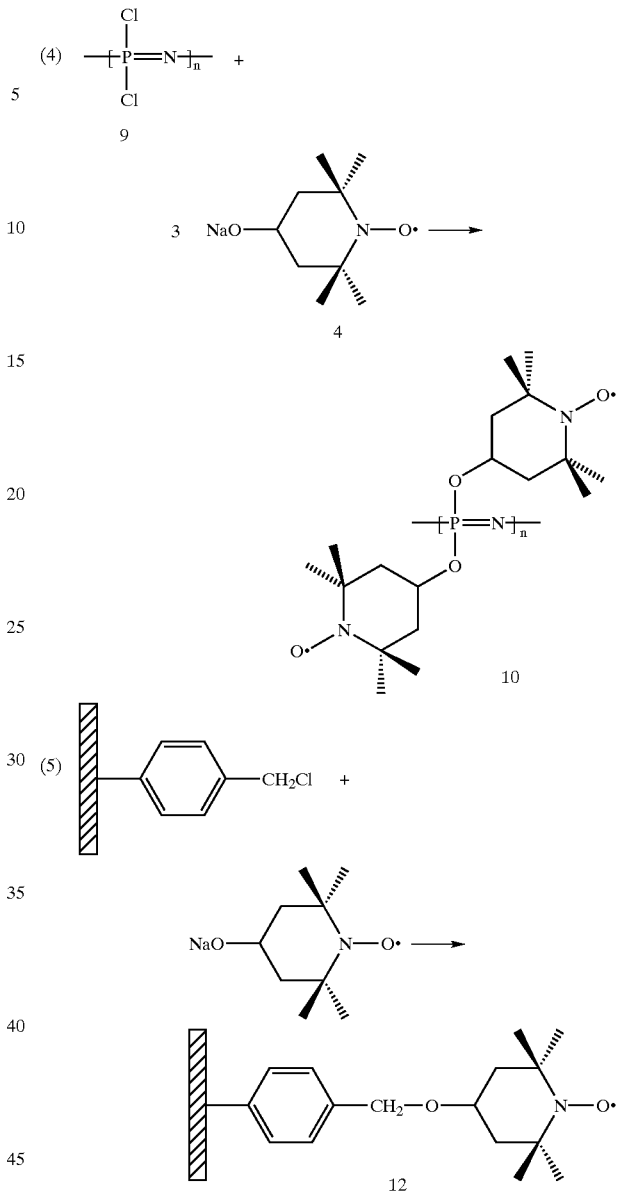

The compounds of formulae (II) and (III) are novel and the invention relates likewise thereto.

The invention relates also to the use, as a catalyst for the selective oxidation of alcohols to ketones by means of an alkali hypohalite under alkaline conditions, of a compound of formula (I), (II), (III) or a 4-oxy-2,2,6,6-tetramethylpiperidin-1-oxyl that is 4-oxy-bound to a Merrifield polymer.

The following Examples illustrate the invention.

EXAMPLES A

Preparation of the Oxidation Catalysts

EXAMPLE A1

Preparation of Compound 6.

In a 500 ml Schlecnk tube, 20 g (113.6 mmol) of 4-hydroxy-TEMPO, compound 3, are dissolved in 200 ml of anhydrous toluene and then 3.34 g (139.2 mmol) of NaH are added thereto in small portions. The reaction batch is stirred for about 12 hours at room temperature and then a solution of 4.75 g (25.75 mmol) of cyanuric chloride, compound 5, in approximately 50 ml of toluene is added dropwise thereto. The solution is stirred first of all at room temperature for 2.5 hours and then at approximately from 70° C. to 90° C. for 72 hours. After cooling to room temperature, the organic phase is washed three times with 100 ml of a 10% aqueous solution of $Na_2CO_3$ each time and then dried over $Na_2SO_4$. All volatile constituents are evaporated off in vacuo at $10^{-2}$ torr and the red oil that remains is recrystallised from a small amount of ethyl acetate, yielding 9.3 g (61%) of product in the form of fine orange-red needles. M.p. 164–166° C. The product is insoluble in $H_2O$ but soluble in $CH_2Cl_2$, $CHCl_3$, $C_6H_5Cl$, toluene and ethyl acetate.

EXAMPLE A2
Preparation of Compound 8.

In a 500 ml Schlenk tube, 20 g (113.6 mmol) of 4-hydroxy-TEMPO, compound 3, are dissolved in 200 ml of anhydrous THF and then 3.34 g (139.2 mmol) of NaH are added thereto in small portions. The reaction batch is stirred for about 12 hours at room temperature and then a solution of 6.26 g (18 mmol) of hexachlorocyclotriphosphazene, compound 7, in approximately 50 ml of THF is added dropwise thereto and the reaction mixture is heated under reflux at 70° C. for approximately 24 hours. After cooling to room temperature, the volatile constituents are evaporated off in vacuo (approximately $10^{-2}$ torr) and the residue is dissolved in 100 ml of $CH_2Cl_2$. The organic phase is washed twice with 50 ml of a 10% aqueous solution of NaOH each time and then three times with approximately 50 ml of $H_2O$ each time. The organic phase is dried with $Na_2SO_4$ and the volatile constituents are evaporated off in vacuo (approximately $10^{-2}$ torr), yielding a pulverulent orange-red solid that is insoluble in $H_2O$ and hexane and relatively readily soluble in THF, $CHCl_3$ and $CH_2Cl_2$.

EXAMPLE A3
Preparation of Compound 10.

In a 500 ml Schlenk tube, 29.62 g (168.3 mmol) of 4-hydroxy-TEMPO, compound 3, are dissolved in 200 ml of THF, and then 5.0 g (208 mmol) of NaH are added thereto. The reaction mixture is stirred at room temperature for 12 hours and then added dropwise to a solution of 5 g (43.1 mmol) of poly(dichlorophosphazene), compound 9, in 100 ml of THF. The reaction mixture is stirred for 12 hours at room temperature and subsequently heated under reflux for two hours, then concentrated to approximately 10% of its volume and poured into ice-water. The precipitated polymer is removed by filtration and treated with ice-water again. The salmon-coloured, pulverulent precipitate is removed by filtration and then washed with a mixture of THF and $H_2O$ (20/80) and subsequently with hexane. The resulting powder is dried in vacuo for approximately 12 hours, yielding 16 g (95.7%) of product, compound 10; m.p.>180° C. Compound 10 is soluble in $CH_2Cl_2$, $CHCl_3$, acetone, THF and toluene; $M_w$ approximately 25000.

EXAMPLE A4
Preparation of Compound 12:

In a 500 ml Schlenk tube, 7 g (40.63 mmol) of 4-hydroxy-TEMPO, compound 3, are dissolved in 120 ml of DMF or THF (freshly distilled). At 0° C., 1.6 g (66.67 mmol) of NaH are added to the solution. The batch is heated to room temperature and then stirred for 1 hour. The reaction solution is subsequently cooled to 0° C. in an ice-bath and 3.5 g of polymer (Merrifield polymer from Fluka, 200–400 mesh, 1% divinylbenzene, 1.7 mmol of Cl/g) are added thereto. The batch is stirred for 30 minutes at 0° C. and then heated to room temperature and stirred for from 1 to 4 days. The batch is subsequently diluted with ice-water, stirred and filtered. The residue is washed with ice-water until the filtrate is colourless. The product is then suspended in toluene and stirred for from 1 to 2 hours in order to remove non-fixed 4-hydroxy-TEMPO. Filtration is then carried out again and the yellow powder is dried in a stream of air.

The powder contains 0.9 mmol of N-oxyl/g.

EXAMPLES B

Oxidation of Alcohols

General procedure for the oxidation of a primary or secondary alcohol a) Preparation of the $NaOCl/NaHCO_3$ solution:

4 ml of a saturated solution of $NaHCO_3$ are mixed with 2 ml of an NaOCl solution (13–14%). The solution is stored in a sealed bottle at 0° C.

b) Oxidation procedure:

1.0 g of the alcohol and 0.25 g of the compound (12) from Example A4 are introduced into a 250 ml round-bottomed flask and then suspended in a mixture of 5 ml of acetone and 15 ml of toluene. The batch is stirred vigorously for from 5 to 10 minutes at room temperature until the alcohol has dissolved and the resin is swollen. The reaction vessel is cooled to 0° C. With vigorous stirring, 6 ml of the $NaOCl/NaHCO_3$ solution prepared in 1) are added and the batch is stirred for 0.5 hours at from 0 to 5° C. The ketone is obtained in almost quantitative yield after conventional working up.

c) Recovery of the catalyst:

If the catalyst is to be used in a plurality of reactions directly following one another, then at the end of each reaction the catalyst is removed by filtration (G3 frit), briefly washed with acetone and immediately re-used. After having been used ten times, no loss of activity can be detected. The catalytic activity of the compound (12) can also be maintained following storage. For that purpose the filtered-off catalyst is washed repeatedly with acetone/toluene, then with water, again with acetone and finally with acetone/toluene (removal of NaOCl, starting material and product). Storage is in the moist state in a securely sealed container.

EXAMPLES B1 and B2
Oxidation of Simple Alcohols:

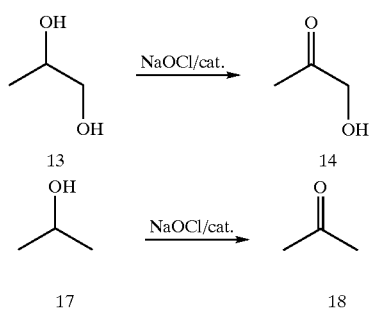

The experiments are carried out as described in the general procedure. The α-hydroxy-ketone 14 is obtained from 13, and the acetone 18 from isopropanol 17, in almost quantitative yield.

EXAMPLE B3
Preparation of α-Hydroxyacetophenone from Phenylglycol:

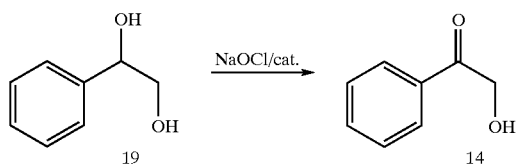

Phenylglycol 19 is reacted as described in the general procedure, with NaOCl in the presence of 5% by weight of 12 as catalyst, to form α-hydroxyacetophenone (20). Product 20 is isolated in almost quantitative yield in the form of a crystalline solid.

EXAMPLE B4
Preparation of Acetylacetone:

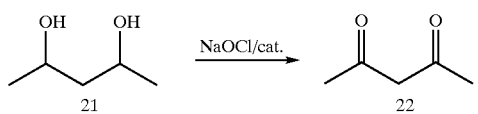

1.0 g of alcohol 21 and 0.25 g of compound 12 are introduced into a 250 ml round-bottomed flask and then 20 ml of toluene are added thereto. The reaction vessel is subsequently cooled to 0° C. With vigorous stirring, 12 ml of the above-described NaOCl/NaHCO$_3$ are added and the batch is stirred at from 0 to 5° C. for ½ hour. The 1,3-diketone 22 is obtained as reaction product in almost quantitative yield.

EXAMPLE B5
Preparation of 2,2,4,6-tetramethyl-1,3-dioxane (23):

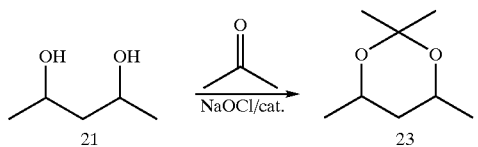

The reaction is carried out as described in Example 4, except that it is carried out in a mixture of 15 ml of toluene and 5 ml of acetone instead of with 20 ml of toluene. 2,2,4,6-Tetramethyl-1,3-dioxane (23) is obtained as reaction product in almost quantitative yield according to gas chromatography.

EXAMPLE 6
Preparation of 2-ethyl-2,4,6-trimethyl-1,3-dioxane (24):

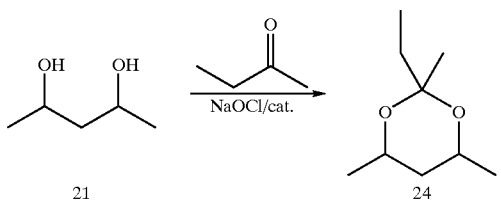

The reaction is carried out as described in Example B4, except that a mixture of 15 ml of toluene and 5 ml of 2-butanone is used instead of 20 ml of toluene. 2-Ethyl-2,4,6-trimethyl-1,3-dioxane (24) is obtained as reaction product in almost quantitative yield.

EXAMPLE B7
Preparation of tetrahydropyran-2-ol (21) and tetrahydropyran-2-one (22)

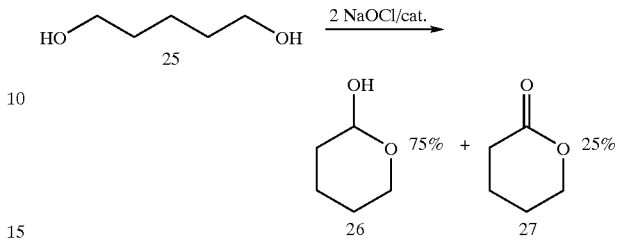

1,5-Pentanediol 25 is oxidised as described in Example B4 with basic NaOCl in the presence of compound 12 as catalyst, except that the oxidising agent, sodium hypochlorite (13% active chlorine), is used stoichiometrically. After a reaction time of 30 minutes, a mixture of 75% compound 26 and 25% compound 27 is obtained.

EXAMPLE B8

Preparation of tetrahydropyran-2-one (27)

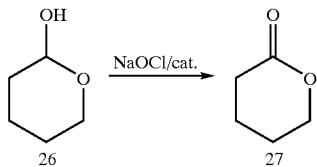

The mixture of 26 and 27 prepared in Example B7 is reacted, as depicted, with excess NaOCl solution buffered to pH 9.0–9.5, 26 being oxidised completely to 27.

EXAMPLE B9

Preparation of 2-(5-hydroxy-pentyloxy)-tetrahydropyran (26)

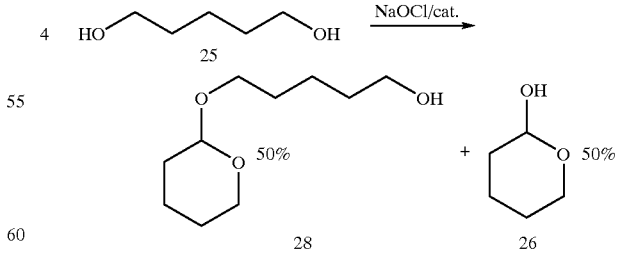

The above-depicted reaction is carried out with a fourfold excess of diol 25 relative to NaOCl. Conventional working up yields a mixture of 50% acetal 28 and 50% tetrahydropyran-2-ol 26.

EXAMPLE B10
Preparation of Benzil (29) from Benzoin:

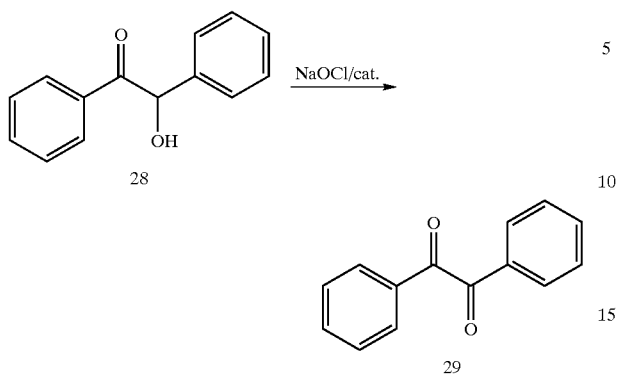

5.0 g (23.5 mmol) of benzoin (28) are reacted as described in the general procedure with sodium hypochlorite in the presence of 1 g of compound 12 at from 0 to 5° C. in 50 ml of toluene/acetone 3:1. During the hypochlorite addition, the solid initially present in the reaction mixture dissolves. When the addition is complete, the batch is stirred for 45 minutes. Monitoring by thin-layer chromatography indicates complete and selective conversion. Conventional working up and subsequent recrystallisation of the crude product from n-hexane yields 4.6 g of benzil (29) (93% of theory).

What is claimed is:

1. A compound of formula III

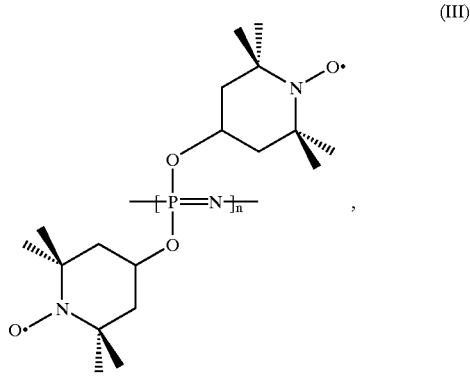

(III)

where n is a number from 3 to 3000.

* * * * *